United States Patent
Liu et al.

(10) Patent No.: US 7,655,918 B2
(45) Date of Patent: Feb. 2, 2010

(54) CMOS IMAGE SENSORS ADAPTED FOR DENTAL APPLICATIONS

(75) Inventors: Xinqiao Liu, San Jose, CA (US); Boyd Fowler, Sunnyvale, CA (US)

(73) Assignee: Fairchild Imaging, Inc, Milpitas, CA (US)

(*) Notice: Subject to any disclaimer, the term of this patent is extended or adjusted under 35 U.S.C. 154(b) by 295 days.

(21) Appl. No.: 11/494,058

(22) Filed: Jul. 26, 2006

(65) Prior Publication Data

US 2008/0024635 A1   Jan. 31, 2008

(51) Int. Cl.
G01T 1/20 (2006.01)
(52) U.S. Cl. .................................. 250/370.11
(58) Field of Classification Search ............. 250/370.11
See application file for complete search history.

(56) References Cited

U.S. PATENT DOCUMENTS

| | | | |
|---|---|---|---|
| 5,434,418 A | 7/1995 | Schick | |
| 5,510,623 A * | 4/1996 | Sayag et al. ........... | 250/370.11 |
| 5,834,782 A | 11/1998 | Schick et al. | |
| 5,852,647 A | 12/1998 | Schick et al. | |
| 5,898,753 A | 4/1999 | Schick et al. | |
| 5,908,294 A | 6/1999 | Schick et al. | |
| 5,912,942 A | 6/1999 | Schick et al. | |
| 5,995,583 A | 11/1999 | Schick et al. | |
| 6,069,935 A | 5/2000 | Schick et al. | |
| 6,134,298 A | 10/2000 | Schick et al. | |
| 6,761,561 B2 | 7/2004 | Mandelkern et al. | |
| D493,892 S | 8/2004 | Royzen et al. | |
| 6,908,307 B2 | 6/2005 | Schick | |
| 6,924,486 B2 | 8/2005 | Schick et al. | |
| 6,972,411 B2 | 12/2005 | Schick et al. | |
| 7,009,646 B1 * | 3/2006 | Fossum et al. ............... | 348/294 |
| 2003/0152196 A1 * | 8/2003 | Bratslavsky et al. ........ | 378/170 |
| 2005/0270084 A1 * | 12/2005 | Lai et al. .................... | 327/514 |
| 2006/0067462 A1 * | 3/2006 | Hack .......................... | 378/38 |

* cited by examiner

*Primary Examiner*—David P Porta
*Assistant Examiner*—Shun Lee
(74) *Attorney, Agent, or Firm*—Calvin B. Ward

(57) ABSTRACT

An image sensor having a two-dimensional array of CMOS pixel sensors, a row decoder and a column decoder is disclosed. The two-dimensional array of CMOS pixel sensors is organized as a plurality of rows and columns that are addressed with the aid of row and column decoders. At least one of the column decoder or the row decoder is located between two of the rows or two of the columns, respectively. X-rays are converted to light that is detected by the image sensor by a layer of scintillation material that overlies the two-dimensional array. The internally located decoder or decoders facilitate sensors in which the two-dimensional array includes a rectangular array having a chamfered corner such that rows or columns that extend into the chamfered corner have lengths that are less than rows or columns, respectively, that do not extend into the corners.

6 Claims, 9 Drawing Sheets

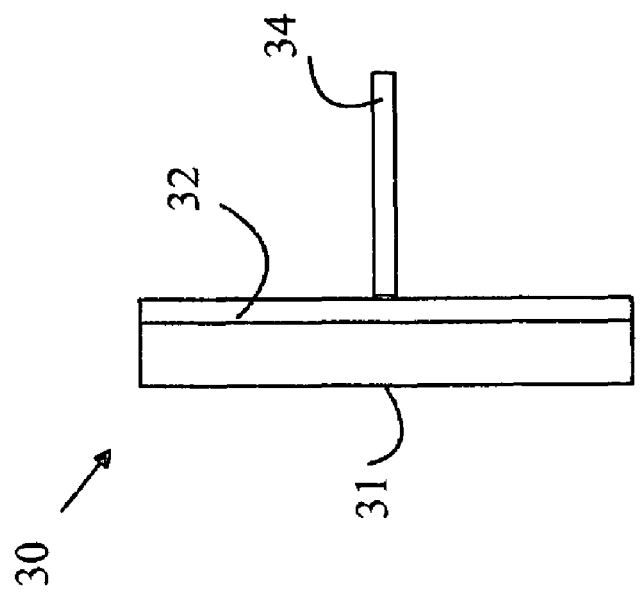
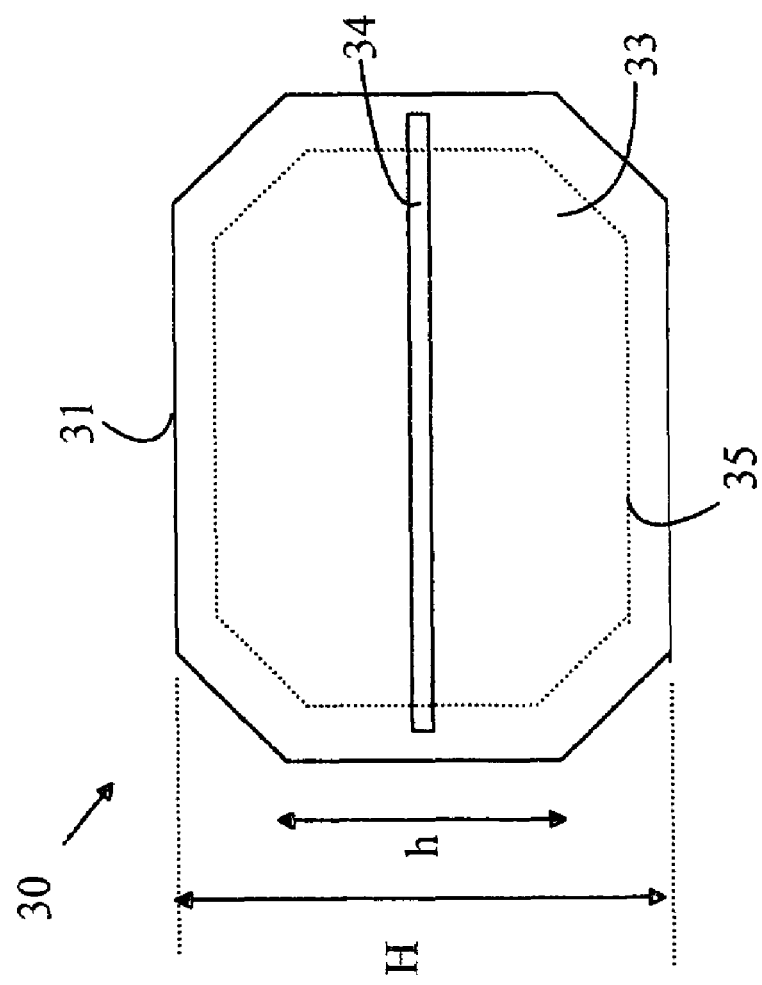

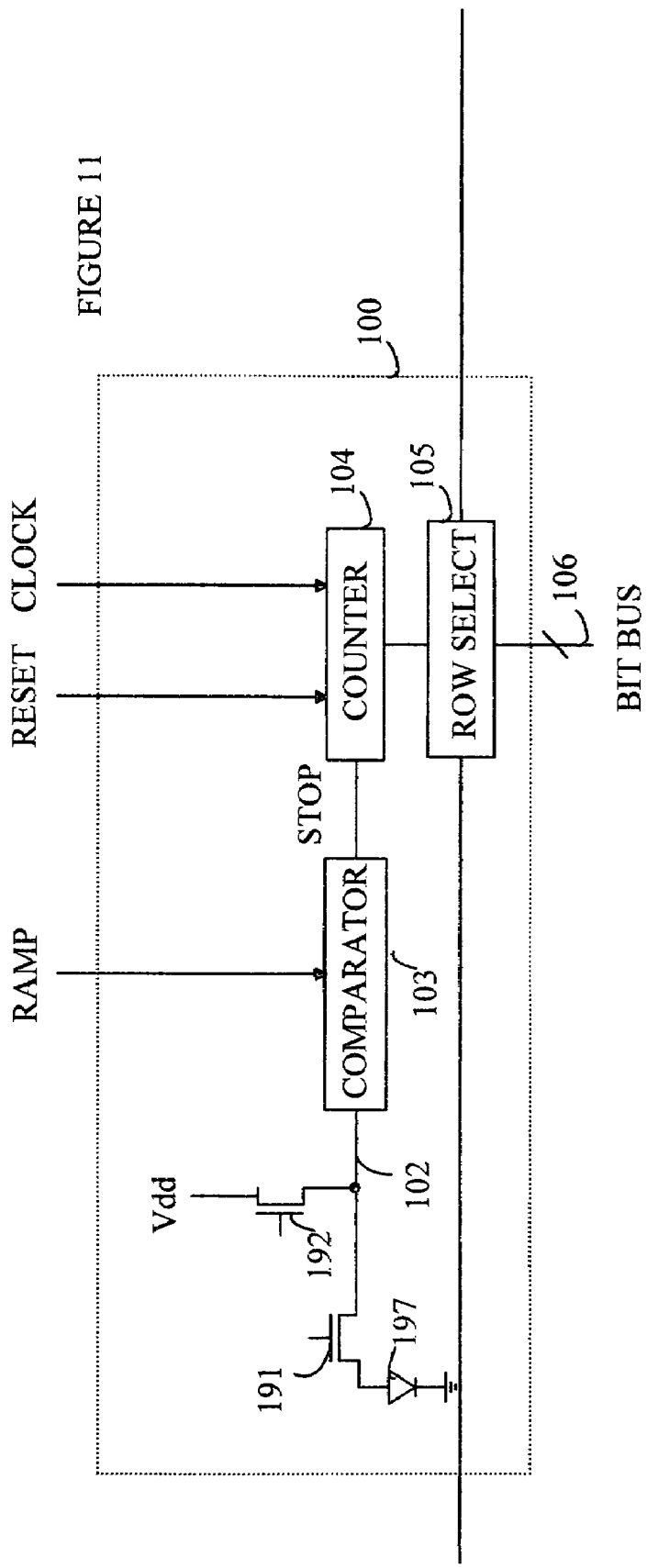

CMOS IMAGE SENSORS ADAPTED FOR DENTAL APPLICATIONS

BACKGROUND OF THE INVENTION

Dental x-rays are typically taken with a film that is placed in the patient's mouth. The film is exposed through the teeth by an x-ray source that resides outside the patient's head. While this method has been in use for many years, it has its disadvantages. First, the patient is exposed to a significant dose of x-rays. This dose is accumulative over the patient's lifetime. Second, the time, cost, and equipment needed to process the film increases the cost of the dental examination. Third, the chemicals utilized in processing the film pose a disposal problem.

These problems have led to several attempts to replace the film component of the traditional x-ray examination with a solid-state sensor that is placed in the patient's mouth to record the x-ray image. In such systems, a layer of scintillation material is used to convert the x-rays to visible light. The visible light is then imaged onto a solid-state imaging array. Since solid-state x-ray sensors of this type are significantly more sensitive to x-rays than the films utilized today, the x-ray dosage can be reduced by typically a factor of 10. In addition, the sensor is re-used, and hence, the cost and disposal problems associated with the conventional x-ray system are avoided. Finally, since the image is in digital form, systems based on solid-state sensors are easily adapted to paperless office systems.

Ideally, the sensor that is placed within the patient's mouth has smooth edges to avoid injury to the patient's gums during the examination. Accordingly, sensors that have chamfered corners are preferred. Unfortunately, conventional solid-state imaging sensors have a shape that is predominately rectangular. This shape is the result of the need to utilize the silicon substrate as efficiently as possible and the conventional processes in which the dies are eventually separated from a wafer by sawing the wafer into rectangular pieces. Hence, to provide a die in which the corners are removed, the die must be made significantly larger to allow the sensor to be located in the interior of the die and still provide sufficient space to cut-off the corners without harming the sensor region.

Sensors having chamfered corners based on CCD imaging arrays are known to the art. For example, U.S. Pat. No. 5,510,623, teaches a CCD x-ray dental sensor with chamfered corners. However, sensors based on CCD arrays are less than ideal for intra-oral x-ray sensors. In particular, CCD sensors are more sensitive to degradation by x-rays than CMOS image sensors. Hence, an x-ray shielding layer is needed between the scintillation layer and CCD array to protect the CCD array from x-rays that are not converted in the scintillation layer. This layer degrades the image. In addition, CCD arrays require relatively high voltages to operate and are more expensive to fabricate than CMOS sensors. Since cost is an important factor in achieving acceptance of a new imaging system by the dental community, these additional costs can be a serious barrier to the introduction of solid-state imaging systems. Hence, it would be advantageous to have an x-ray imaging system based on a CMOS image sensor.

SUMMARY OF THE INVENTION

The present invention includes an image sensor having a two-dimensional array of CMOS pixel sensors, a row decoder and a column decoder. The two-dimensional array of CMOS pixel sensors array are organized as a plurality of rows and columns. The pixel sensors in each column are connected to a corresponding bit bus by a row select switch that connects the pixel sensor in the row to that bit bus in response to a row select signal on a corresponding row select line. The row decoder generates the row select signal on a selected one of the row select lines in response to a row address that is coupled thereto. The column decoder connects a selected one of the bit buses to an interface connecting the image sensor to a circuit that is external to the image sensor. One of the column decoder or the row decoder is located between two of the rows or two of the columns, respectively. X-rays are converted to light that is detected by the image sensor by a layer of scintillation material that overlies the two-dimensional array. In one aspect of the invention, the two-dimensional array includes a rectangular array having a chamfered corner such that the rows or columns that extend into the chamfered corner have lengths that are less than the rows or columns, respectively, that do not extend into the corners.

BRIEF DESCRIPTION OF THE DRAWINGS

FIG. 2 is a top view of the desired configuration for a dental sensor.

FIG. 3 is a side view of the desired configuration for a dental sensor.

FIG. 11 is a schematic drawing of a pixel cell that utilizes a distributed ADC according to one embodiment of the present invention.

DETAILED DESCRIPTION OF THE PREFERRED EMBODIMENTS

Figure 1:
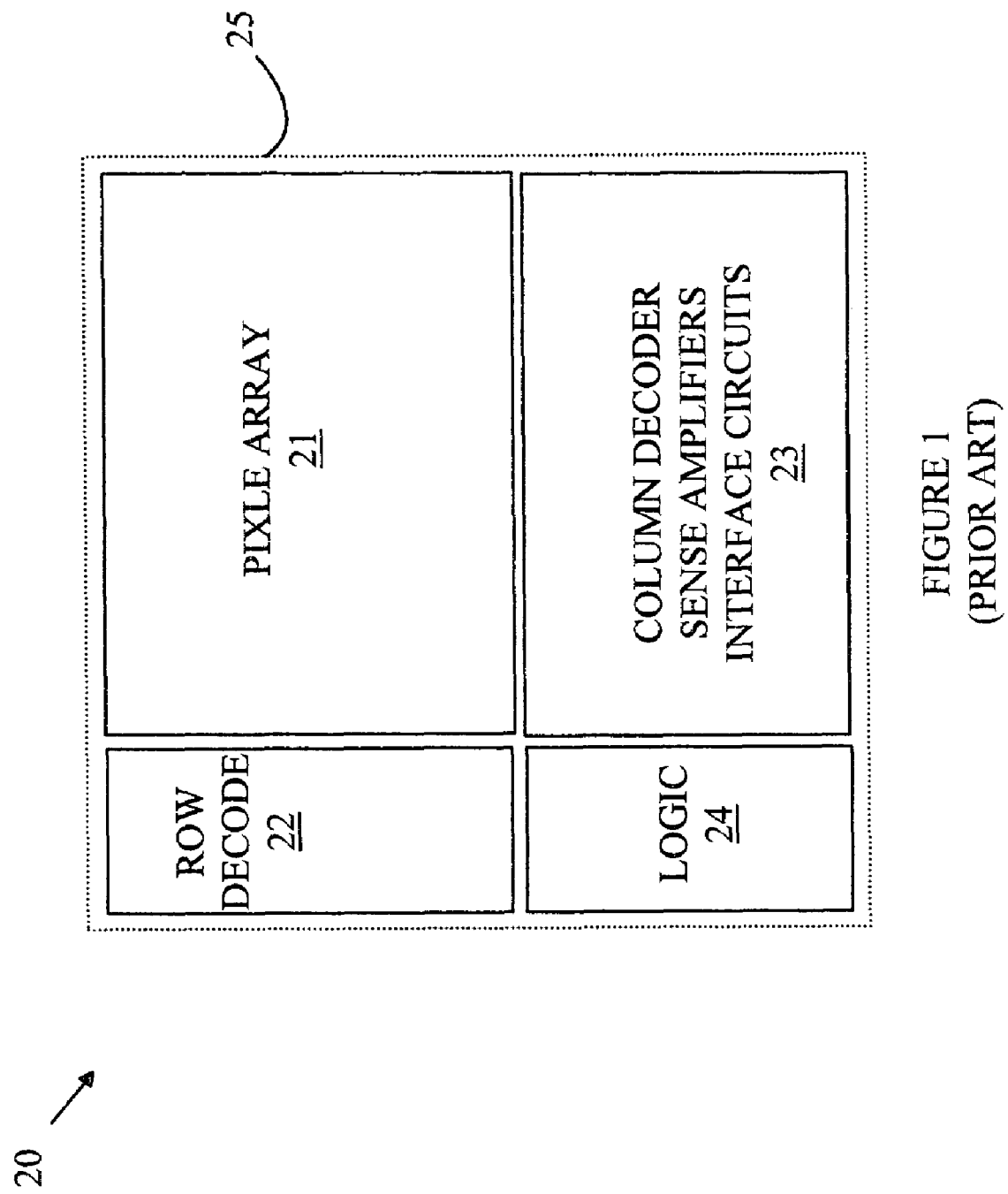
FIG. 1 is a block diagram of a prior art conventional CMOS image sensor.

The manner in which the present invention provides its advantages can be more easily understood with reference to FIG. 1, which is a block diagram of a prior art conventional CMOS image sensor. CMOS image sensor 20 includes a two-dimensional pixel array 21, which is the active area for image measurement, and some peripheral circuits that do not contribute to image sensing. These, circuits generally include a logic controller 24, and row and column decoders 22 and 23. The individual pixels are read out over bit lines that terminate in a row decoder/sense amplifier. Sensor die 25 is normally rectangular, and the pixel array normally does not extend to all four edges of the die.

Light from the image generates a charge signal inside each pixel. After a fixed integration time, the pixel charge signals are read out from the array and are eventually digitized to form a digital image. The readout of the pixel array is facilitated by the row and column decoders, and operates much like a digital memory readout. The row decoder selects a row of pixels at a time. Each pixel's output in that row is connected to a corresponding bit line that is shared by a column of the pixels. The column decoder connects one pixel signal at a time to the output until it finishes all the pixels in that row. The row decoder then selects the next row of pixels in the array, and the readout procedure repeats until the whole array is read out. In a conventional CMOS image sensor layout, the row and column decoder are located outside the 2D pixel array; the row decoder has the same height as the array, and the column decoder has the same width as the array.

The problems inherent with the conventional CMOS design shown in FIG. 1 when that design is used to construct a dental sensor can be more easily understood with reference to FIGS. 2 and 3, which illustrate the desired configuration for a dental sensor. FIG. 2 is a top view of sensor 30, and FIG. 3 is a side view of sensor 30. Sensor 30 is preferably constructed on a single die 31 with the imaging array 33 positioned in the middle of the die. The sensor utilizes a scintillation layer 32 to convert the x-rays to visible light that is recorded by imaging array 33. The sensor is positioned in the patient's mouth with the aid of a member 34 that is gripped between the teeth of the patient. The height, H, of the sensor must be sufficient to cover both the upper and lower teeth of the patient, but not so large as to cause the patient discomfort when the patient bites down on member 34. As noted above, the corners of the sensor are preferably chamfered to prevent patient discomfort arising from a sharp corner being forced against the patient's gums or one of the soft surfaces in the patient's mouth.

Refer again to FIG. 1. One method for adapting imaging array 21 for use in dental sensor 30 would be to use an imaging array that has the boundary shown at 35 in FIG. 2 with the remaining circuitry distributed in the area outside of boundary 35. However, as noted above, the row and column decoders must be the same width and height, respectively, as the imaging array. Hence, unless the imaging array is reduced to a height h, this constraint cannot be accommodated. A similar problem applies to the column decoder along one of the horizontal edges of die 31. If the imaging array is so reduced, the border region will be too large to provide the necessary image height. In addition, the wasted space on the edges that are not used for the column and row decoders or other circuitry substantially increases the cost of the sensor.

Figure 4:
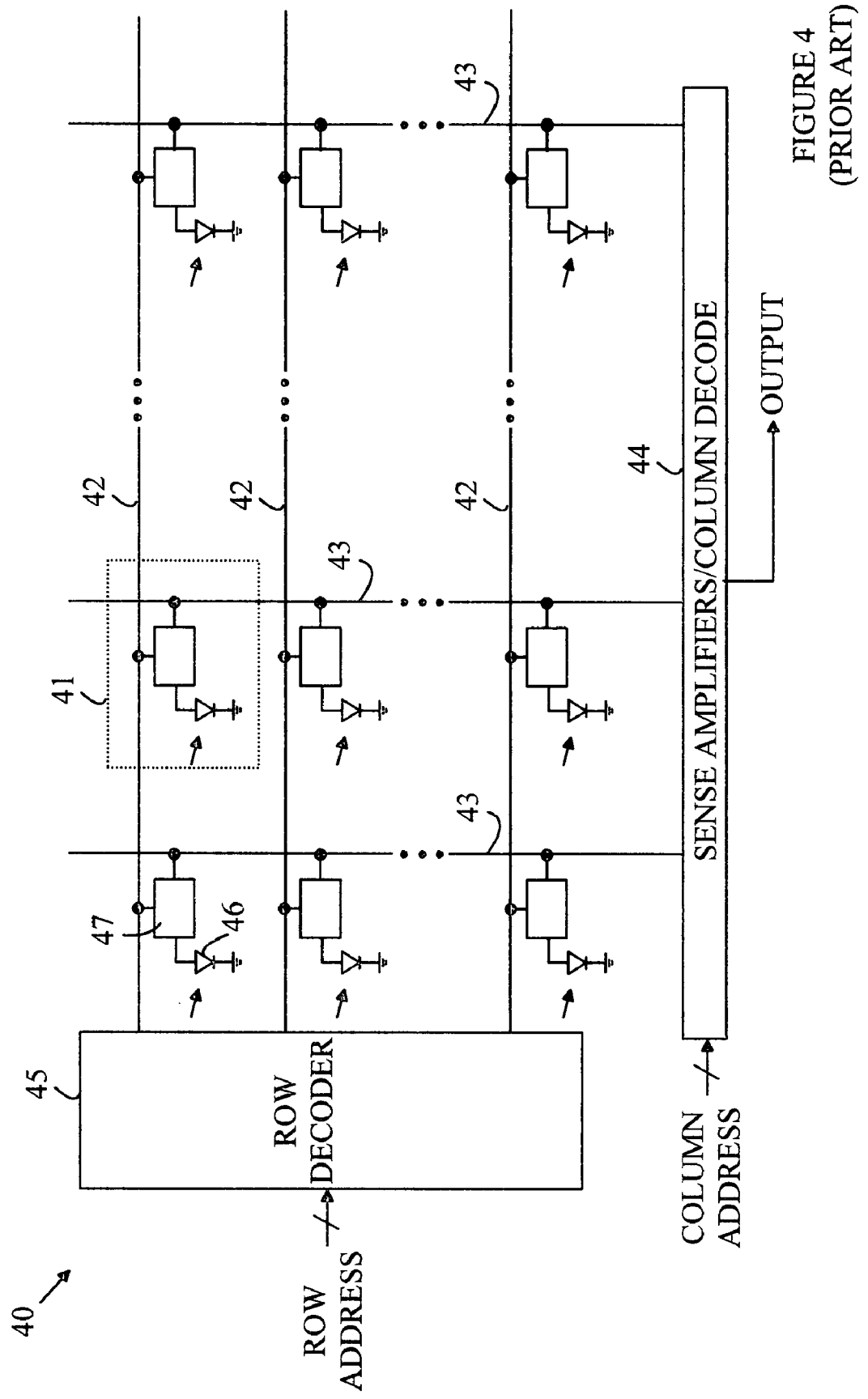
FIG. 4 is a block diagram of a prior art CMOS imaging array.

Refer now to FIG. 4, which is a block diagram of a prior art CMOS imaging array. Imaging array 40 is constructed from a rectangular array of pixel cells 41. Each pixel cell includes a photodiode 46 and an interface circuit 47. The details of the interface circuit depend on the particular pixel design. However, all of the pixel circuits include a gate that is connected to a row line 42 that is used to connect that pixel to a bit line 43. The specific row that is enabled at any time is determined by a bit address that is input to a row decoder 45. The row select lines are a parallel array of conductors that run horizontally in the metal layers over the substrate in which the photodiodes and interface circuitry are constructed. As noted above, row decoder 45 has a length that is equal to that of the vertical dimension of the pixel array, since all of the row conductors must terminate on the row decoder.

The various bit lines terminate in a column processing circuit 44 that typically includes sense amplifiers and column decoders. The bit lines are a parallel array of conductors that run vertically in the metal layers over the substrate in which the photodiode and interface circuitry are constructed. Each sense amplifier reads the signal produced by the pixel that is currently connected to the bit line processed by that sense amplifier. The sense amplifiers may generate a digital output signal by utilizing an analog-to-digital converter (ADC). At any given time, a single pixel cell is readout. The specific column that is readout is determined by a column address that is utilized by a column decoder to connect the sense amplifier/ADC output from that column to circuitry that is external to the imaging array. As noted above, the width of the column decoder is the same as the width of the imaging array, since all of the bit lines must terminate on the column decoder.

Figure 5:
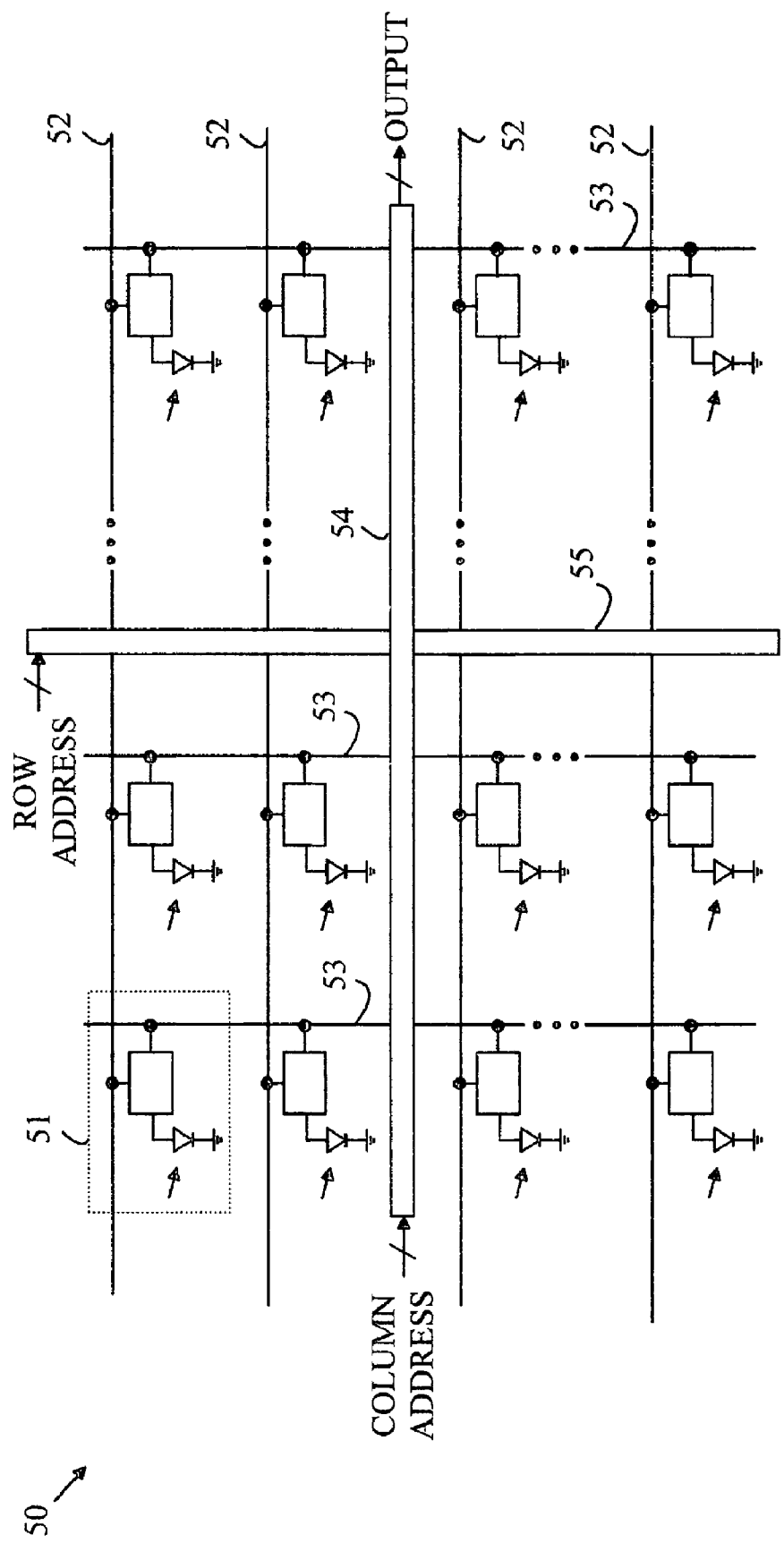
FIG. 5 illustrates a pixel array according to one embodiment of the present invention.

The present invention overcomes these problems by placing the row and column decode circuitry in the interior of the pixel array at locations such that the decode circuitry can extend the full width and height of the pixel array even when the corners of the pixel array are chamfered. Refer now to FIG. 5, which illustrates a pixel array according to one embodiment of the present invention. Pixel array 50 includes a plurality of pixel cells 51 that operate in a manner analogous to cells 41 discussed above. Pixel array 50 also includes a row decoder 55 and a column decoder 54 that includes the sense amplifiers discussed above. The row decoder selects the pixels in one row at a time that are to be connected to the bit lines shown at 53 by placing a select signal on one of the row lines shown at 52. However, the row and column decoders are located within the body of the pixel array.

Since the row and column decoders are located within the pixel array, a column and a row of pixels are displaced within the array. The sensor having pixel array 50 is intended for placement in the mouth in a manner in which the sensor is held in position by the patient biting down on a tab that is approximately at the center of the pixel array. Since there are no teeth to image at the location of the tab, the displacement of a few rows in the center of the pixel array is of little consequence.

It should be noted that the row decoder requires significantly less space than the column decoders that must also include other circuitry such as the sense amplifiers. Hence, the row encoder typically will require only the displacement of a single row of pixels. The size of the area that is lost is small compared to the resolution needed to provide a useable x-ray image. Hence, any lost pixels can be re-created by interpolating the pixel values on each side of the displaced column.

The above-described embodiments show the row/column address lines and the column decoder output in the same plane as the decoder circuitry. However, this is only for illustrative purposes. In practice, the relevant conductors are located in the metal layers over the decode circuitry.

Figure 6:
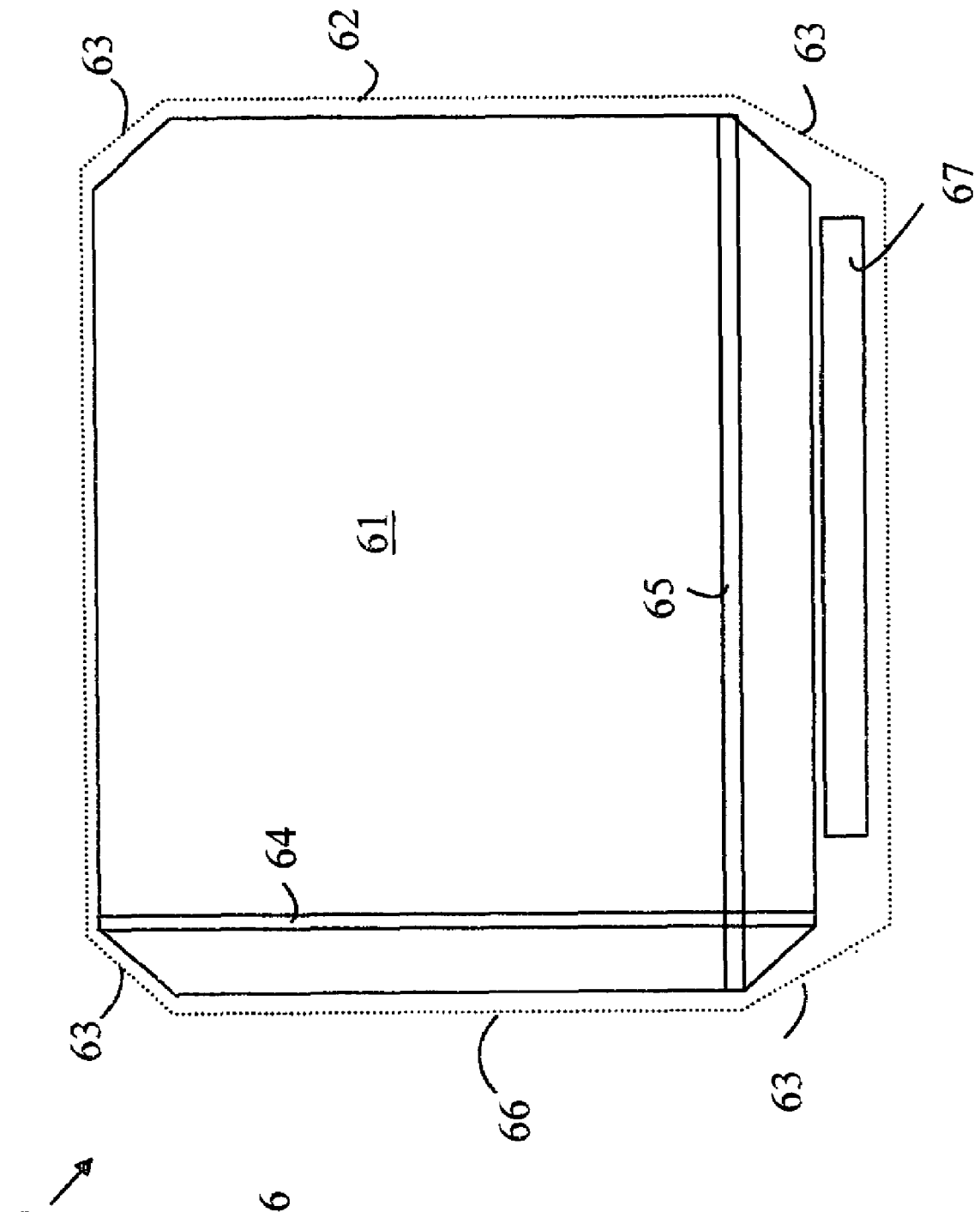
FIG. 6 illustrates another embodiment of a pixel array chip according to the present invention.

While the above-described embodiments utilize a pixel array with the decoders in the middle of the array, other arrangements can be utilized so long as the decoders are placed at a location in which the decoders can extend over the entire array width and length. Refer now to FIG. 6, which illustrates another embodiment of a pixel array chip according to the present invention. Pixel array chip 60 is constructed on a die 62 whose corners 63 have been chamfered for patient comfort. Pixel array chip 60 includes a pixel array 61 having a plurality of rows and columns of CMOS photodiode elements that are addressed via a row encoder 64 and a column encoder 65 that includes the sense amplifiers for reading the output of the individual pixel elements. Row encoder 64 is placed as close to edge 66 as possible and still span the entire height of pixel array 61. Similarly, column encoder 65 is placed as close as possible to the bottom edge of die 62 and still span the entire width of pixel array 61. The additional logic circuits are placed in the silicon substrate in region 67, which is laid out on active layers of the substrate and metal layers that overlie the substrate. The input-output pads for connecting pixel array chip 60 to external circuitry are deposited on the two top most metal layers over region 67.

Figure 7:
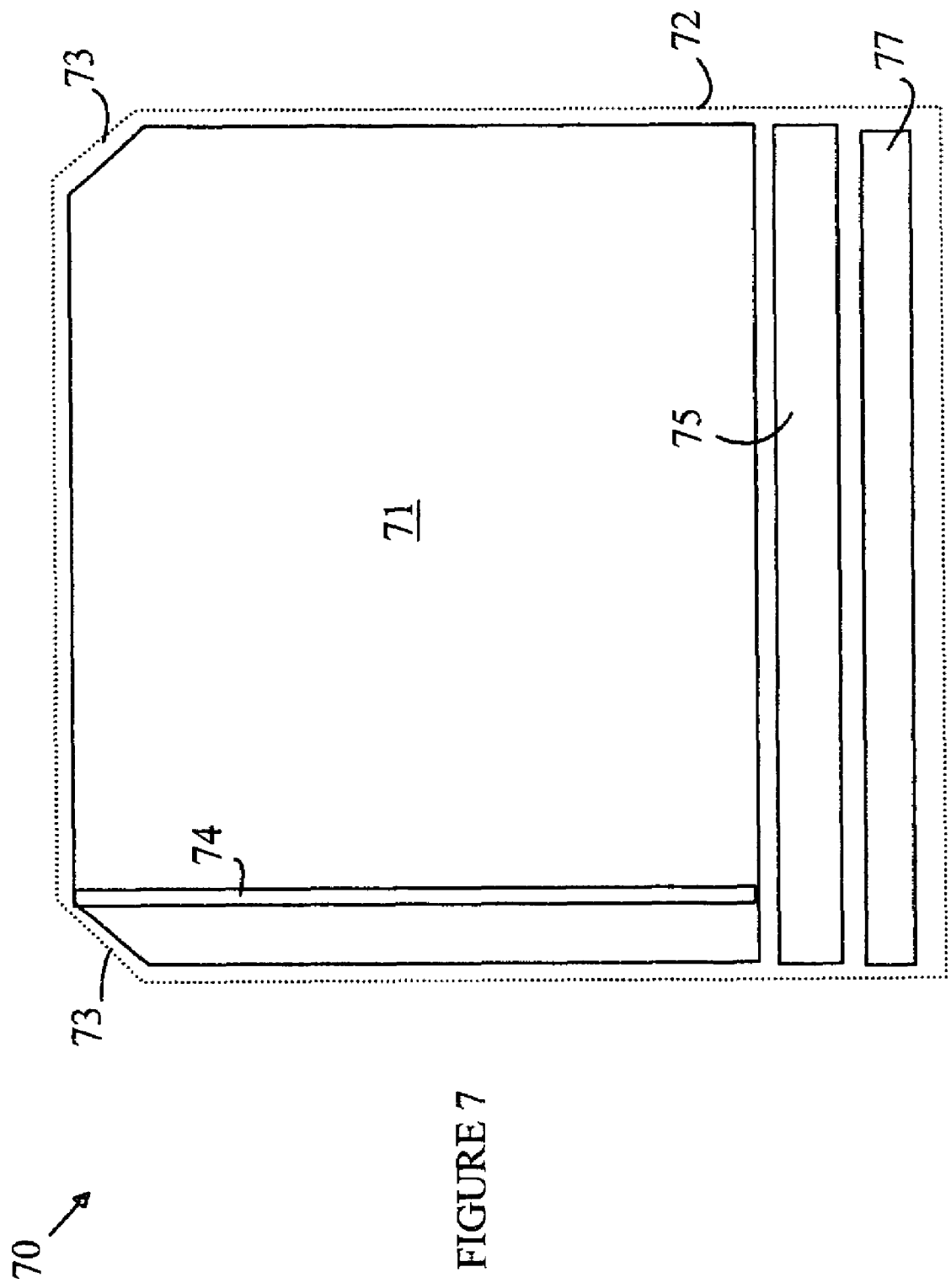
FIG. 7 illustrates another embodiment of a pixel array chip according to the present invention.

The size of the pixel array chip is sufficiently large that in some embodiments of a dental sensor according to the present invention, two chips are preferred to reduce the die size. In this case, only two of the corners on each chip need to be chamfered. Refer now to FIG. 7, which illustrates another embodiment of a pixel array chip according to the present invention. Pixel array chip 70 includes a pixel array 71 on a die 72. Pixel array 71 has a plurality of rows and columns of photodiode elements that are addressed by a row decoder 74 and a column decoder 75 that includes the sense amplifiers used for reading the output of the individual pixel elements that are connected to the bit lines within pixel array 71. The additional circuitry and input/output pads are located in region 77 in a manner analogous to that described above with respect to pixel array chip 60 shown in FIG. 6.

Figure 9:
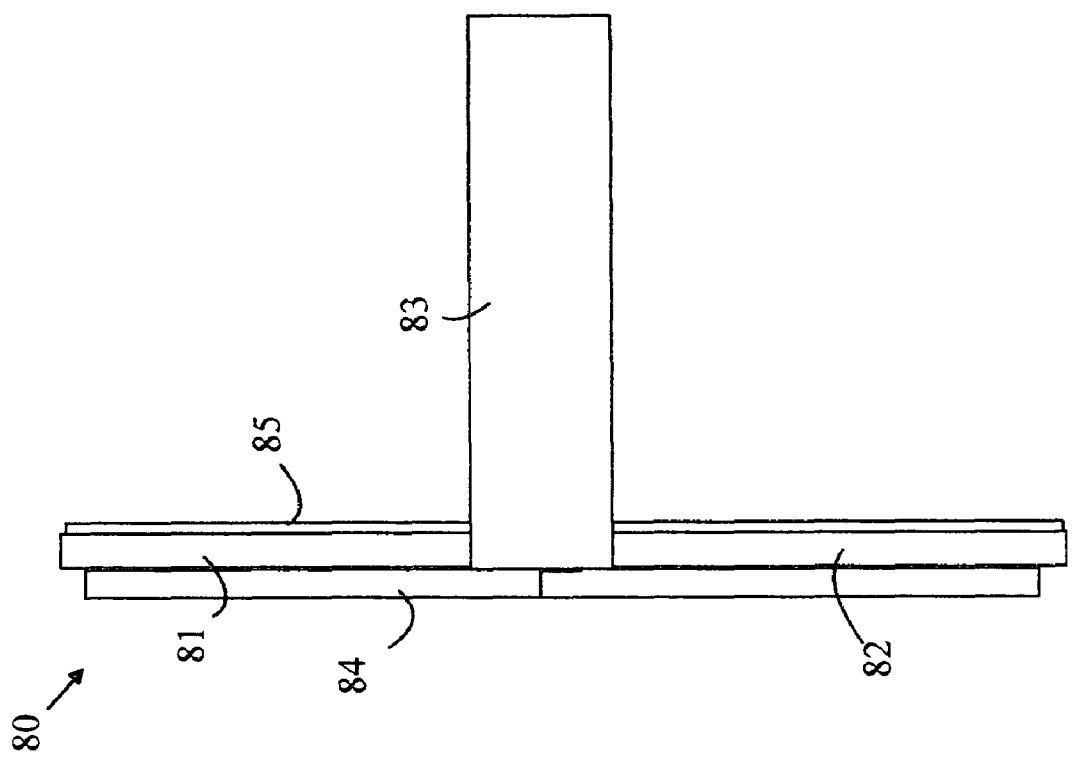
FIG. 9 is a side view of dental sensor 80.
Figure 8:
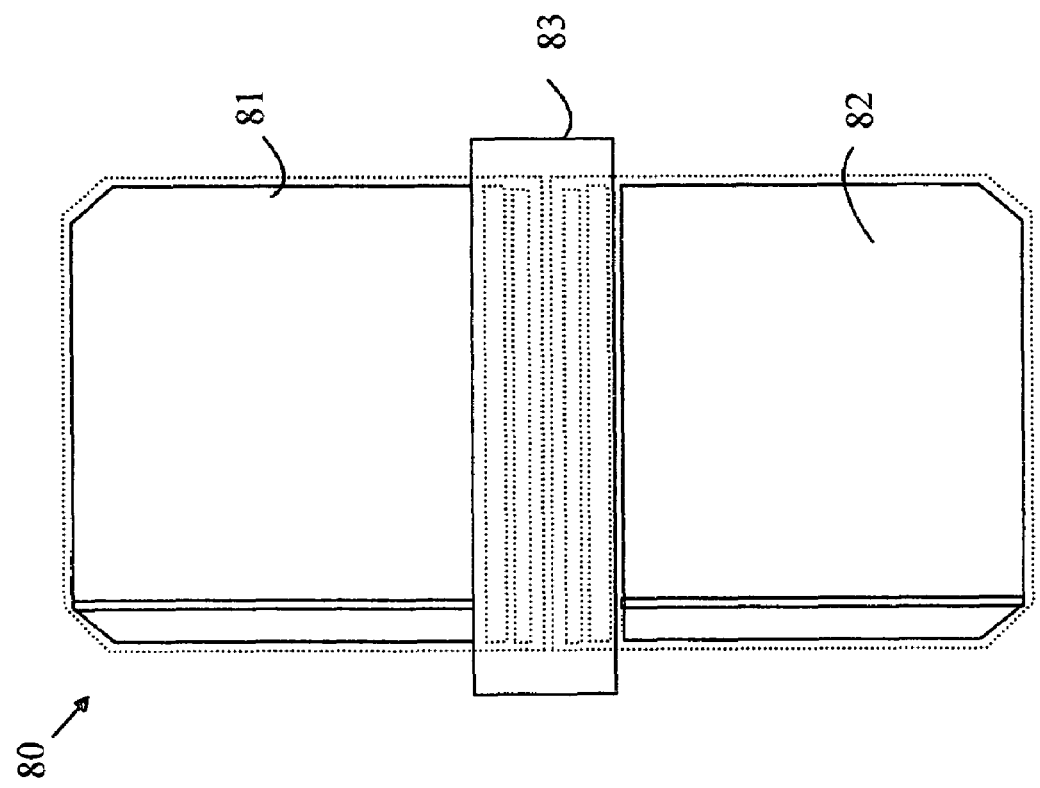
FIG. 8 is a top view of dental sensor 80.

Chip 70 is designed to be butted to another chip of the same configuration to form a dental sensor. Refer now to FIGS. 8 and 9, which illustrate a compound dental sensor constructed from two such pixel array chips. FIG. 8 is a top view of dental sensor 80, and FIG. 9 is a side view of dental sensor 80. Dental sensor 80 includes pixel array chips 81 and 82, which are bonded to a substrate 84 that includes a tab 83 that is gripped between the patient's teeth during the x-ray procedure. A layer of scintillation material 85 is bonded to the top surface of the pixel array chips to convert the x-rays into visible photons that are detected by the photodiodes in the pixel arrays.

Refer again to FIG. 7. Since only two corners of each pixel array chip can come into contact with the roof or floor of the patient's mouth, only these corners need to be chamfered as shown at 73. Hence, the column decoder and the associated sense amplifiers can be placed outside of pixel array 71. Row decoder 74 is again placed within pixel array 71 as near to the left edge of pixel array 71 as possible and still provide a row decoder that spans the height of pixel array 71.

As noted above, the pixel elements in the pixel array are arranged in a rectangular array of rows and columns. In the regions that terminate on the chamfered corners, the rows and columns are terminated at or near the boundary of the die; however, the pixel arrangement is still one of rows and columns.

In the embodiments discussed above, the pixel array is chamfered by making a linear cut to remove the corners in question. However, other forms of removing the corners can be utilized. For example, a boundary that is a portion of a regular polygon is well adapted to semiconductor fabrication lines.

Figure 10:
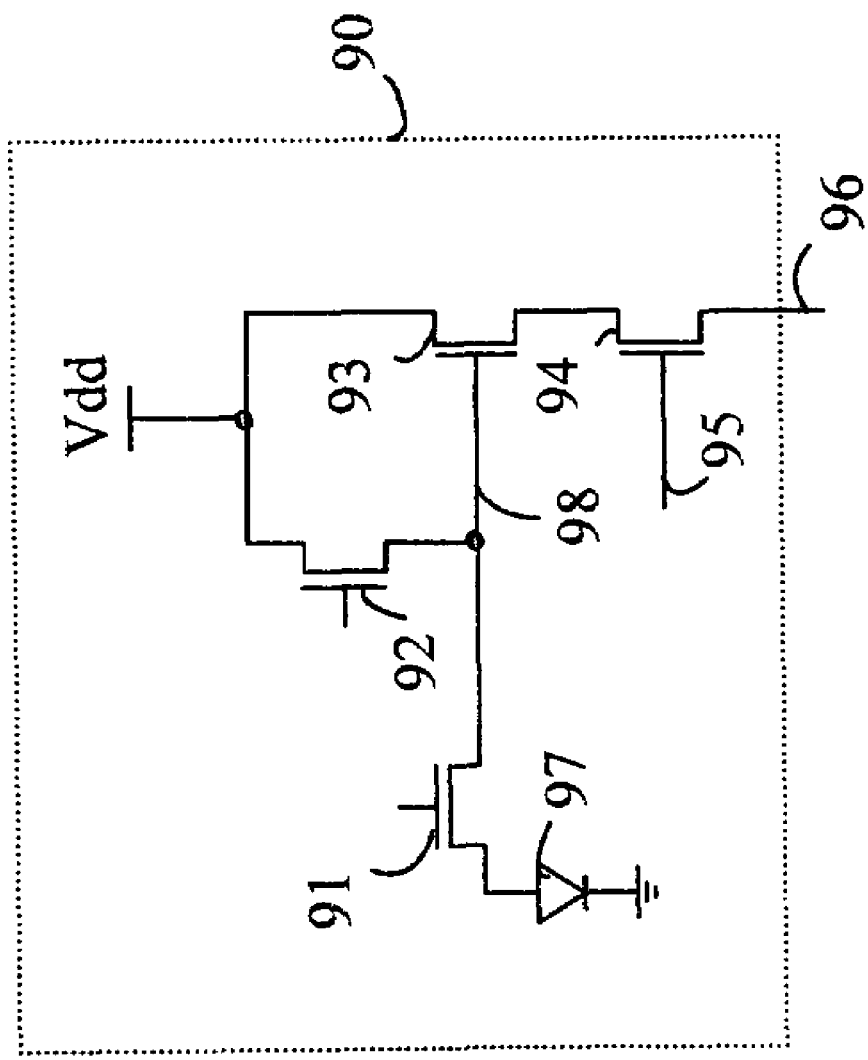
FIG. 10 is a schematic drawing of one embodiment of a pixel element that can be utilized in the present invention.

As noted above, each pixel element includes a photodiode and processing circuitry that allows the charge stored on that photodiode to be connected to a bit line at the time the pixel element is readout. The nature of this processing circuitry depends on the particular image sensor design. Refer now to FIG. 10, which is a schematic drawing of one embodiment of a pixel element that can be utilized in the present invention. Pixel 90 includes four transistors 91-94 in each pixel along with the photon-sensing element such as photodiode 97. Photodiode 97 is a pinned photodiode. Transistor 92 is a reset transistor that is used to set a fixed voltage on node 98 prior to the pixel accumulating charge. Transistor 91 is used to transfer the charge from the photodiode to node 98 after the image has been recorded. Transistor 93 acts as a source follower to provide the drive current needed to transfer the signal to bit line 96. Transistor 94 is a gate that connects the pixel to the bit line in response to a signal on the row line 95.

In one embodiment of the present invention, the sense amplifier/ADC function is distributed within the pixel array to further reduce the amount of circuitry that must be placed in the column decoder circuit block discussed above. In a conventional x-ray imaging system, the charge accumulated by each photodiode is converted into a voltage signal and amplified at the pixel level and transferred to the bit lines. The signal from each pixel is further amplified at the end of the bit lines by the sense amplifiers and the amplified signal is then digitized to provide a digital light value corresponding to each pixel.

This approach has two problems. First, the signal transferred on the bit lines is relatively small and subject to noise. To reduce the noise, the speed at which the signal is readout is reduced, which increases the readout time. Second, the circuitry associated with the sense amplifier and analog to digital converters requires a significant amount of space. This space must be allocated either at the edge of the pixel array or in the space that includes the column decoder. In either case, the space that must be allocated to this circuitry reduces the number of rows of pixels.

In one embodiment of the present invention, these problems are overcome by utilizing space within each pixel that is not needed for the photodiode area. The size of each pixel is determined by two factors. First, the pixel must be large enough to accommodate a photodiode that has sufficient area to detect the photons generated in the scintillator when the teeth are exposed to an acceptable level of x-rays. While reducing x-ray exposure is desirable, there is a point at which a still larger photodiode is not needed since the level of exposure is already significantly below the level currently used in conventional dental x-ray examinations and deemed to be safe.

Second, the size of each pixel is determined by the resolution in the x-ray image. Reducing the size of each pixel below some minimum size determined by the resolution in the optical image generated by the scintillator does not provide a significant improvement in the resolution of the image of the teeth. The resolution is determined by the scintillator and the distance between the teeth and the image sensor. In the case of a CMOS x-ray sensor, the optimum pixel size is of the order of 25 microns on a side. That is, providing a pixel array in which each pixel is smaller than this size and increasing the number of pixels to fill the image area does not result in a significantly better image. Of this pixel area, a small reduction of the photodiode area, i.e., less than 10 percent, will not affect the pixel signal integrity noticeably. This leaves a sufficient area of silicon that can be utilized for other circuitry. In this embodiment, this space is used to construct a portion of the circuitry that would normally reside in the sense amplifier/ADC/row decoder block, and hence, reduce the circuitry and area needed to implement the sense amplifier/ADC/row decoder block.

In particular, a "distributed ADC" and memory are constructed in each pixel. The charge accumulated by the pixel is digitized in the pixel by the ADC and stored in the memory. The contents of the memory are then readout over the "bit lines". As a result, the sense amplifier/ADC/row decoder block does not need to include the analog sense amplifiers and ADC circuitry. Hence, less space is required for this block.

Refer now to FIG. 11, which is a schematic drawing of a pixel cell that utilizes a distributed ADC according to one embodiment of the present invention. Pixel cell 100 includes a photodiode 197 that is connected to a gate transistor 191 and a reset transistor 192 that operate in a manner analogous to that described above. After the pixels in the array containing pixel cell 100 have been exposed, the charge on each of the photodiodes is digitized. At the start of the digitization process, the charge stored on photodiode 197 is coupled to node 102 by applying a signal to gate 191. The counter is then reset and begins to count clock pulses while the potential on the other input of the comparator 103 (RAMP signal) is increased. The potential on the ramp line is linearly (or exponentially if dynamic range compression is implemented)

related to the count that has accumulated in counter 104. When the ramp potential is equal to the potential at node 102, the comparator 103 generates a stop signal that is applied to counter 104. Hence, counter 104 is left with a count that is related to the potential at node 102. After all of the pixels have been digitized in this manner, the pixels are readout one row at a time using a row decoder that operates a set of row select switches 105 that connect the counter output to a bit bus 106, which serves a function analogous to the bit lines described above. In this embodiment, the bit bus includes one line per bit in counter 104. Hence, the counter is readout in parallel down bit bus 106. While this embodiment utilizes a bit bus that reads out the counter bits in parallel, embodiments in which the bits in the counter are shifted down a single conductor bit line can also be constructed.

The circuitry for generating the ramp signal and clock signals can be located in the column decoder or row decoder areas or the areas shown at 77 in FIG. 7 or 67 in FIG. 6.

While the above embodiments utilize a count up ADC, other forms of ADC could be utilized. For example, the comparator could trigger when the ramp becomes less than the signal generated by the photodiode. In this case, the ramp starts at a high value and decreases with time. Similarly, the counter could be replaced by a latch in which the bits are set using a successive approximation method for digitizing the signal from the photodiode.

The above-described embodiments utilize an arrangement in which the columns in the imaging array are approximately perpendicular to the gap between the patient's upper and lower rows of teeth. However, embodiments in which the image sensor is turned by 90 degrees such that the rows are approximately perpendicular to this gap can also be constructed. Furthermore, the terms row and column are arbitrary and thus could be interchanged.

The embodiments of the present invention described above utilize a photodiode to convert the light incident on each pixel to a charge. However, other forms of photosensor such as a phototransistor could be utilized.

Various modifications to the present invention will become apparent to those skilled in the art from the foregoing description and accompanying drawings. Accordingly, the present invention is to be limited solely by the scope of the following claims.

What is claimed is:

1. A dental imaging element comprising:
   a substrate having four chamfered corners;
   a two-dimensional array of CMOS pixel sensors located on said substrate, said array being organized as a plurality of rows and columns, said pixel sensors in each column being connected to a corresponding bit bus by a row select switch that connects said pixel sensor in said row to that bit bus in response to a row select signal on a corresponding row select line;
   a row decoder that generates said row select signal on a selected one of said row select lines in response to a row address being coupled thereto;
   a column decoder that connects a selected one of said bit buses to an interface connecting said dental imaging element to a circuit that is external to said dental imaging element; and
   a layer of scintillation material overlying said two-dimensional array, said scintillation material emitting light in response to x-rays impinging thereon;
   wherein said two-dimensional array of CMOS pixel sensors extends into said chamfered corners, and
   wherein said row decoder and said column decoder are located between two of said columns and two of said rows, respectively, such that said row decoder and said column decoder do not extend into any one of said chamfered corners.

2. The dental imaging element of claim 1 further comprising a tab extending outward from said two-dimensional array and positioned such that when a patient bites on said tab, said dental imaging element is positioned in a predetermined relationship to said patient's teeth.

3. The dental imaging element of claim 2 wherein said tab is located over said column decoder, said tab covering said column decoder.

4. The dental imaging element of claim 1 wherein said pixel sensors comprise:
   a photosensor;
   a comparator that compares a voltage generated by said photosensor with a reference voltage, said comparator generating a stop signal when said reference signal is in a predetermined relationship with said voltage;
   a counter that counts pulses from a clock input until said stop signal is generated, said counter storing a digital count value; and
   a gate circuit connected to one of said row select lines that transfers said digital count value to said bit bus corresponding to that pixel sensor in response to a signal on that row select line.

5. A dental imaging element comprising:
   a rectangular substrate having four chamfered corners;
   a first two-dimensional array of CMOS pixel sensors located on said substrate, said array being organized as a plurality of rows and columns, said pixel sensors in each column being connected to a corresponding bit bus by a row select switch that connects said pixel sensor in said row to that bit bus in response to a row select signal on a corresponding row select line;
   a first row decoder that generates said row select signal on a selected one of said row select lines in said first two-dimensional array of CMOS pixel sensors in response to a row address being coupled thereto;
   a first column decoder that connects a selected one of said bit buses in said first two-dimensional array of CMOS pixel sensors to an interface connecting said dental imaging element to a circuit that is external to said dental imaging element;
   a second two-dimensional array of CMOS pixel sensors located on said substrate, said second array being organized as a plurality of rows and columns, said pixel sensors in each column of said second array being connected to a corresponding bit bus by a row select switch that connects said pixel sensor in said row of said second array to that bit bus in response to a row select signal on a corresponding row select line;
   a second row decoder that generates said row select signal on a selected one of said row select lines of said second array in said second two-dimensional array of CMOS pixel sensors in response to a row address being coupled thereto; and
   a second column decoder that connects a selected one of said bit buses in said second two-dimensional array of CMOS pixel sensors to said interface; and
   a layer of scintillation material overlying said first and second first two-dimensional array of CMOS pixel sensors,
   wherein said first two-dimensional array of CMOS pixel sensors extends into two of said four chamfered corners, and said first column decoder and said first row decoder do not extend into said two of said four chamfered corners; and wherein said second two-dimensional array of CMOS pixel sensors extends into two others of said four chamfered corners, and said second column decoder and said second row decoder do not extend into said two others of said four chamfered corners.

6. The dental imaging element of claim 5, further comprising a tab extending outward from said two-dimensional arrays and positioned such that when a patient bites on said tab, said dental imaging element is positioned in a predetermined relationship to said patient's teeth, wherein said tab is positioned between said first and second two-dimensional arrays.

* * * * *